United States Patent [19]
Gahara et al.

[11] Patent Number: 4,950,239
[45] Date of Patent: Aug. 21, 1990

[54] ANGIOPLASTY BALLOONS AND BALLOON CATHETERS

[75] Inventors: William J. Gahara, Nashua; Thomas R. Johnson, Milford, both of N.H.; Tilak M. Shah, Guilford, Conn.

[73] Assignee: Worldwide Medical Plastics Inc., Nashua, N.H.

[21] Appl. No.: 230,251

[22] Filed: Aug. 9, 1988

[51] Int. Cl.⁵ ............................................. A61M 25/10
[52] U.S. Cl. ..................................................... 604/96
[58] Field of Search ............... 604/280, 53, 99, 100, 604/101, 96; 128/348.1

[56] References Cited

U.S. PATENT DOCUMENTS

| | | | |
|---|---|---|---|
| 4,448,195 | 5/1984 | LeVeen et al. | 604/100 |
| 4,456,000 | 6/1984 | Schjeldahl | 604/53 |
| 4,456,011 | 6/1984 | Warnecke | 604/101 |
| 4,840,623 | 6/1989 | Quackenbush | 604/180 |

Primary Examiner—David J. Isabella
Attorney, Agent, or Firm—St. Onge Steward Johnston & Reens

[57] ABSTRACT

Angioplasty and related medical dilatation balloons are molded from a polyurethane in which the "soft" segment is a minor segment by weight and the "hard" segment is the major segment by weight and which polyurethane has a hardness of at least 75D and a glass transition temperature of more than about 38° C. The balloons can be integrally molded on one end of a catheter fabricated from the above type of polyurethane. Alternatively, the balloon is formed from polyurethane of the above type and the catheter is formed from elastomeric polyurethane and like polymers commonly employed in preparation of catheters. The balloon is then bonded to the catheter by conventional procedures.

15 Claims, 2 Drawing Sheets

ANGIOPLASTY BALLOONS AND BALLOON CATHETERS

BACKROUND OF THE INVENTION

1. Field of the Invention.

invention relates to balloons and to balloon catheters which are useful in medical dilatation procedures and is more particularly concerned with high pressure medical dilatation balloons and balloon catheters fabricated from a particular type of polyurethane.

2. Description of the Prior Art.

Balloon catheters are finding increasing use in medical procedures such as percutaneous transluminal angioplasty, percutaneous transluminal nephrostomy, ureteral dilatation, biliary duct dilatation, percutaneous transluminal renal angioplasty, and the like. Balloons for use in these procedures have been prepared from a variety of polymeric materials which are blood and/or tissue compatible. Balloons prepared from relatively elastic materials such as polyvinyl chloride, polyethylene and the like homopolymers or copolymers of olefins, have been found to have disadvantages in practice because of leakage and/or bursting under high pressures of the order of 100 psi or higher, when conducting medical procedures with such balloons. Further, the balloons are normally prepared from a polymeric material which is different from, and is not readily bonded to, the material employed to fabricate the catheter to one end of which the balloon has been attached. In practice, it is found that the balloon can separate from the catheter due to the weakness of the bond between them. This leads to difficulties in removing the balloon from the artery or like vessel which is being subjected to dilatation. Surgery may be required to remove the balloon in such instances.

U.S. Pat. No. 4,448,195 and 4,637,396 describe balloons reinforced with fabric to permit controlled expansion. U.S. Pat. 4,608,984 and 4,646,742 show balloons having multilayer construction seeking to yield controlled expansion amongst other properties.

Levy U.S. Pat. 4,490,421 describes balloons fabricated from polyethylene terephthalate (PET) and related materials which balloons are said to be capable of controlled expansion and to resist bursting at relatively high pressures, up to 500 psi using wall thicknesses as high as 0.048 mm. While these balloons are therefore free from the major hazards due to uncontrolled expansion they are subject to certain disadvantages. Thus, PET is recognized to be a difficult material to mold satisfactorily. More particularly, it is difficult to achieve a satisfactory bond between PET and other elastomeric polymers from which the catheter to be attached to the PET balloon is generally fabricated in the art. Accordingly the possibility of separation of the PET balloon from the catheter during the dilatation procedure still exists as discussed above.

It has now been found that balloons, for use in dilatation procedures, which are free from the disadvantages discussed above can be prepared using a particular type of polyurethane which will be described hereinbelow.

SUMMARY OF THE INVENTION

It is an object of the invention to provide balloons for use in medical dilatation procedures such as angioplasty and the like, which balloons are capable of limited, controlled expansion and which will withstand satisfactorily the pressures to which they may be subjected in said dilatation procedures.

It is a further object of the invention to provide balloon catheters for use in dilatation procedures such as angioplasty and the like, which balloon catheters are free from any tendency for the balloon to separate from the catheter during said procedures.

These objects, and other objects which will become apparent from the description which follows, are achieved by the balloons and balloon catheters of the invention and by the methods for their preparation. Thus, in its broadest aspect, the invention comprises balloons and balloon catheters for use in medical dilatation procedures wherein the balloons have been molded using a polyurethane which has a hardness of at least about 75D, a glass transition temperature of more than about 38° C. and which comprises the reaction product of (a) an organic diisocyanate;
(b) a polyol having an average functionality of at least 1.9 and a molecular weight in the range of about 500 to about 20,000; and
(c) at least one chain extender having a functionality from 2 to 3 and a molecular weight from about 50 to about 400;

said polyurethane being further characterized in that the proportion by weight of said polyol in said polyurethane is from about 2 to about 25 percent.

In a particular embodiment the balloon is integrally molded on one end of a catheter fabricated from a polyurethane meeting the above specifications. In another embodiment of the invention the balloon fabricated from a polyurethane meeting the above specifications is bonded to one end of a catheter fabricated from an elastomeric polyurethane or other polymeric material commonly employed in the art to fabricate catheters.

DETAILED DESCRIPTION OF THE INVENTION

Figure 1:
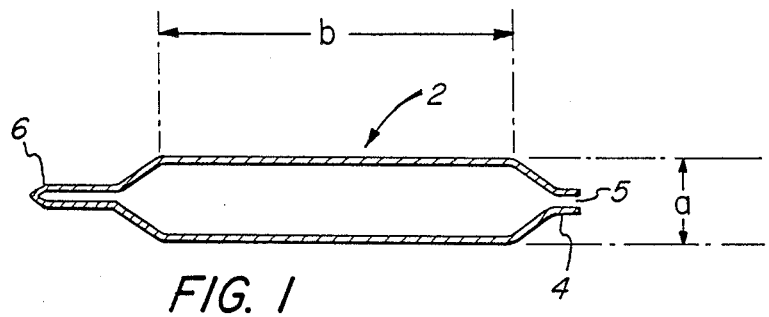
FIG. 1 shows, in cross-section, a typical balloon in accordance with the invention.

The principal novelty in the balloons and balloon catheters of the invention lies in the use in their fabrication of a particular type of polyurethane. The latter comprises a thermoplastic polyurethane which is characterized by high flexural modulus, i.e. a flexural modulus of at least about 150,000 psi up to about 250,000 psi and higher, a glass transition temperature (Tg) of greater than 38 ° C. and, preferably, greater than 75° C. and which, in contrast to thermoplastic polyurethanes commonly employed in fabricating catheters and like medical devices, is also characterized by a high ratio of "hard" segments to "soft segments". Illustrative of polyurethanes of this type are those which are available commercially from Dow Chemical Company under the trademark ISOPLAST, a particularly preferred species for use in the present invention being that which is designated ISOPLAST 301. The composition and method of preparation of these materials is described in Goldwasser et al. U.S. Pat. No. 4,376,834, the disclosures of which are incorporated herein by reference.

The '834 patent describes polyurethanes of the above type which are derived by reaction of (a) an organic diisocyanate, (b) an isocyanate-reactive material having a functionality of at least 1.9, a glass transition temperature (Tg) of less than 20° C. and a molecular weight in the range of about 500 to about 20,000 and (c) at least one chain extender of functionality 2 to 3 and molecular weight from about 50 to about 400. Unlike other thermoplastic polyurethanes known in the art, the polyurethanes of the '834 patent are prepared using only from about 2 to 25 percent, preferably only about 4 to 15 percent, by weight of the isocyanatereactive material (b). It is the latter material which gives rise to "soft" segments in the polyurethane and the extender which gives rise to the "hard" segments.

The polyurethanes of the above type which are employed in the present invention are those which have a hardness of at least about 75D, a glass transition temperature of more than about 38° C., a molecular weight of at least about 150,000, and a flexural modulus in the range of about 150,000 to about 400,000 psi.

Materials having the above properties are fabricated using any of the diisocyanates set forth in the aforesaid U.S. Pat. No. 4,376,834. Advantageously the diisocyanate is selected from toluene diisocyanate (the 2,4 - or 2,6 isomer or mixtures thereof), 4,4' -methylenebis (cyclohexylisocyanate), and 4,4'-methylenebis (phenyl isocyanate) or modified forms thereof. Preferably the diisocyanate is 4,4' -methylenebis (phenyl isocyanate), or modified forms thereof such as that available from Dow Chemical Company under the trademark ISONATE 143L, as the polyisocyanate.

The isocyanate-reactive material (b) used in combination with this polyisocyanate can be any of those set forth in the aforesaid '834 patent but is advantageously a polyol and preferably a polyetherpolyol or a polycaprolactone having a molecular weight in the range of about 500 to about 6000 and a functionality of 2 to 3. The chain extender (c) employed in combination with the above polyisocyanate and polyol is advantageously an aliphatic diol or a mixture of two or more such diols. Illustratively, the extender is 1,6-hexanediol, 1,4-cyclohexanedimethanol, Bisphenol A or a mixture of any two or all of these extenders. A preferred combination of extenders is a mixture of 1,6-hexanediol and 1,4-cyclohexanedimethanol.

The proportion of "soft" segments derived from the component (b) in the polyurethane is advantageously in the range of about 2 to about 50 percent preferably in the range of about 2 to about 25 percent and, most preferably, in the range of about 4 to 15 percent by weight. The method of preparation of the polyurethanes derived from the above combination of materials is advantageously that described in detail in the aforesaid '834 patent.

The balloons and balloon catheters of the invention are prepared in a conventional manner using conventional equipment but employing the particular type of polyurethane discussed above, of which that available from Dow Chemical Company under the trademark ISOPLAST 301 is typical. For example, in producing a typical dilatation balloon of the invention shown overall as (2) in cross-section in FIG. 1, a tube (4) having a wall thickness of about 0.05 mm. to about 0.5 mm. and an internal diameter of about 0.8 mm. to about 10 mm. is formed by extrusion of the aforesaid polyurethane using conventional melt extrusion equipment. One end of the tube is then inserted into a mold having an internal configuration corresponding to the external configuration of the desired balloon. The tube (4) is pinched off at one end (6), the mold is heated above the softening temperature of the polyurethane (in the range of about 60° C. to about 150° C.) and a suitable fluid such as nitrogen is used to pressurize and inflate the softened portion of the tube and force the walls thereof into contact with the walls of the mold.

The actual dimensions of the balloon (2) so formed will depend upon the particular dilatation procedure for which the balloon and any attached catheter are to be employed. In general, where the balloon is to be used in angioplasty the external diameter (a) of the balloon will be of the order of about 2 mm. to about 25 mm. The overall length (b) of the inflated portion will be of the order of about 10 mm. to about 150 mm. The walls of the balloon will have an average thickness in the range of about 0.01 mm. to about 0.2 mm depending in part on the pressures to which the balloon is to be inflated in actual use. However, it is to be understood that these dimensions are given for purposes of illustration only and are not to be construed as limiting.

Figure 2:
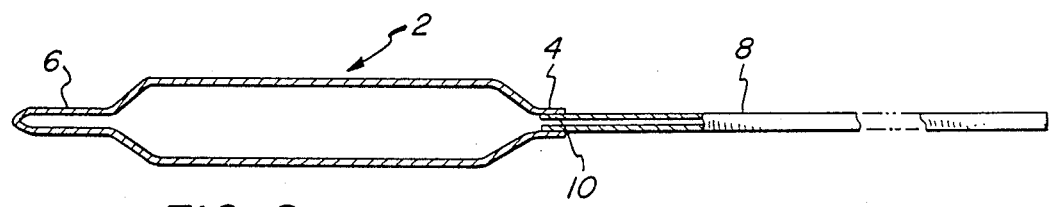
FIG. 2 shows, in partial cross-section, a balloon and attached catheter in accordance with the invention.

FIG. 2 illustrates in cross-section a balloon as shown in FIG. 1 mounted on the distal end (10) of a catheter (8). The latter is advantageously formed from a conventional elastomeric polyurethane employed in the fabrication of catheters. Illustrative of such polyurethanes is that available under the trademarks ESTANE and PELLETHANE from B. F.Goodrich and Dow Chemical Company, respectively However, any of the polymeric materials such as polyvinyl chloride, styrenic polymers such as KRATON ®, polyacrylates, polyolefins, polyamides, polyesters, fluoropolymers, silicones, and the like conventionally employed in the art to prepare catheters, can be employed to fabricate the catheter (8) by extrusion and like means. The union of the balloon (2) and the distal end (10) of catheter (8) is achieved by inserting the distal end (10) into the balloon opening (5) to form an overlap of the order of about 2 mm. and thereafter sealing the abutting surfaces to each other using heat welding, solvent welding, ultrasonic welding, hot melt bonding, adhesive bonding using one or two part solid adhesives, and like conventional techniques.

In the embodiment shown in FIG. 2 the end (10) of catheter (8) is inserted into the open end (5) of balloon (2). As will be readily apparent to one skilled in the art, the sealing of the balloon and catheter can also be carried out by employing a catheter with an outside diameter, at least at the end thereof which is to be used in the formation of the seal, such that the end of the catheter can be mounted over the open end (5) of the balloon (2). Sealing of the abutting surfaces is then carried out in the same manner described for the embodiment of FIG. 2.

Figure 3:
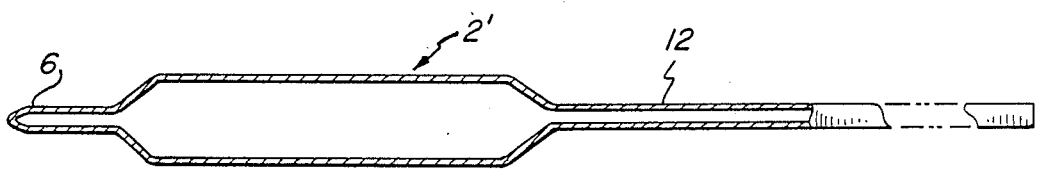
FIG. 3 shows, in partial cross-section, a balloon and catheter in accordance with the invention.

FIG. 3 illustrates another mode of forming a balloon with attached catheter in accordance with the invention. In this embodiment the balloon (2') is molded directly onto the end of catheter (12) which latter has itself been fabricated from the particular polyurethane which is used to form the balloons of the invention. The method of molding can be that described above in connection with the embodiment shown in FIG. 1. The end or tip (6) of the balloon (2') in the embodiment of FIG. 3, like the same feature in balloon (2) in the embodiment of FIG. 2, is preferably tapered and rounded at its extremity. The embodiment of FIG. 3 has the advantage that the balloon and catheter are formed as a single, integral unit thus avoiding the necessity to form the balloon and catheter separately and then bond them together.

Figure 4:
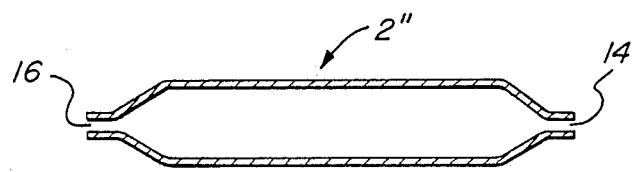
FIG. 4 shows, in cross-section, another typical balloon in accordance with the invention.
Figure 5:
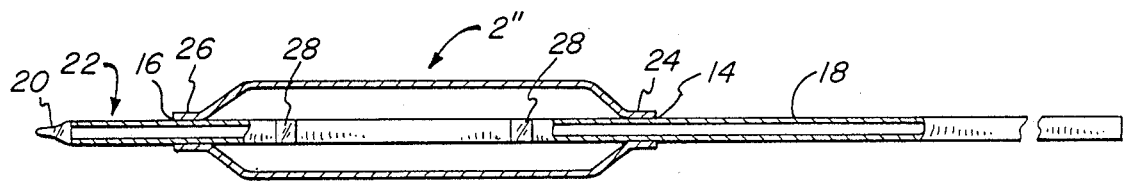
FIG. 5 shows, in partial cross-section, another embodiment of a balloon and attached catheter in accordance with the invention.

FIG. 4 shows another embodiment of a balloon shown overall as (2") in accordance with the invention in which the balloon has openings (14) and (16) at each end thereof. A balloon having this configuration is advantageously fabricated from a balloon of the configuration shown in FIG. 1 by removal of the tip (6) therefrom or, alternatively, can be molded directly from a polyurethane of the type discussed above by injection molding and like conventional techniques. The balloon of FIG. 4 is then mounted on catheter (18) as shown in FIG. 5 by insertion of the tip (20) of catheter (18) into opening (14) and out through opening (16) so that a predetermined portion (22) of the distal end of the catheter (18) protrudes from the balloon. The length of portion (22) can be varied over a wide range depending upon the desired use and method of functioning of the balloon catheter so formed. The abutting surfaces of catheter (18) and flanges (24) and (26) of balloon (2") are then bonded as described above in relation to the embodiment of FIG. 2. Catheter (18) is fabricated from any of the polymeric materials described above in relation to catheters (8) and (12). Catheter (18) is provided with radiopaque bands (28) and radiopaque tip (20) fabricated from radiopaque materials such as platinum and gold. These elements serve to monitor by x-ray the location of the tip (20) and the balloon (2") during a medical dilatation procedure and to ensure that the balloon is located in the desired area of an artery or like vessel or duct before the balloon is inflated.

Figure 6:
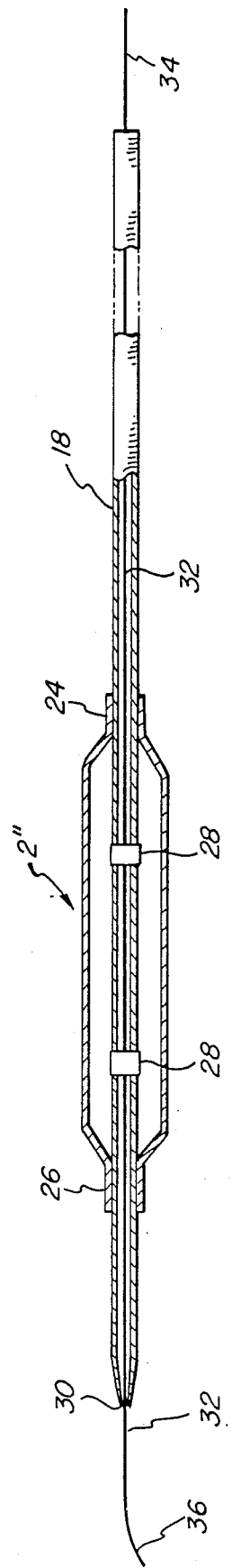
FIG. 6 shows, in partial cross-section, yet another embodiment of a balloon and attached catheter in accordance with the invention.

FIG. 6 shows, in partial cross-section, a modification of the balloon catheter of FIG. 5. In this modification a flexible guide wire (32) traverses the length of catheter (18) in sliding engagement therewith and protrudes from the distal tip (30) of the catheter. The protruding tip (36) of the guide wire (32) is rounded. The inner end (34) of guide wire (32) is received in a torque device (not shown) or like means conventionally employed in the art for manipulating the guide wire during the medical dilatation procedure for which the balloon catheter is to be employed.

As will be obvious to one skilled in the art, the dilatation balloons of the invention can also be employed to replace dilatation balloons in any of the many other types of balloon-catheter combinations, with or without guide wires, currently employed in medical dilatation procedures. The balloons of the invention possess properties which render them especially valuable in carrying out medical dilatation procedures such as angioplasty and the like. Thus, the walls of the balloon are sufficiently thin to allow the balloon to be collapsed by deflation sufficiently to permit passage into and through the artery, vein or like passageway involved in the procedure. However, the walls of the balloon are possessed of sufficient flexural strength such that the balloon will not expand beyond the originally molded configuration under pressures up to at least about 100 psi or significantly higher depending upon the wall thickness and/or overall size of the balloon. Hence there is no problem of uncontrolled expansion or danger of bursting under pressure conditions routinely involved in angioplasty and like procedures. Further, because the balloons can be integrally molded on catheters of the same material as that used for the balloon or, alternatively, can be securely bonded without difficulty to other materials employed in the formation of catheters, there is little or no risk of rupture at the junction of balloon and catheter while the dilatation procedure is being carried out. Accordingly, the balloons and balloon catheters of the present invention represent a significant advance in the art.

What is claimed is:

1. A medical dilatation balloon molded from a polyurethane which has a hardness of at least about 75D and a glass transition temperature of more than about 38° C. and which comprises the reaction product of
   (a) an organic diisocyanate;
   (b) a polyol having an average functionality of at least 1.9 and a molecular weight in the range of about 500 to about 20,000; and
   (c) at least one chain extender having a functionality from 2 to 3 and a molecular weight from about 50 to about 400;
said polyurethane being further characterized in that the proportion by weight of said polyol in said polyurethane is from about 2 to about 25 percent.

2. A medical dilatation balloon in accordance with claim 1 wherein the amount of said polyol is within the range of about 4 to about 15 percent by weight based on the weight of said polyurethane.

3. A medical dilatation balloon in accordance with claim 1 wherein the organic diisocyanate comprises 4,4'-methylenebis (phenyl isocyanate).

4. A medical dilatation balloon in accordance with claim 1 wherein the chain extender comprises an aliphatic diol.

5. A medical dilatation balloon in accordance with claim 1 wherein the chain extender is selected from the class consisting of 1,6-hexanediol, 1,4-cyclohexanedimethanol, Bisphenol A and mixtures of two or all of these compounds.

6. A medical dilatation balloon in accordance with claim 4 wherein the chain extender is a mixture of 1,6-hexanediol and 1,4-cyclohexanedimethanol.

7. A medical dilatation balloon catheter comprising a catheter and a balloon sealingly bonded on or proximate the distal end of said catheter, characterized in that said balloon is fabricated from a polyurethane which has a hardness of at least about 75D, a glass transition temperature of more than about 38° C. and which comprises the reaction product of
   (a) an organic diisocyanate;
   (b) a polyol having an average functionality of at least 1.9 and a molecular weight in the range of about 500 to about 20,000; and
   (c) at least one chain extender having a functionality from 2 to 3 and a molecular weight from about 50 to about 400;
said polyurethane being further characterized in that the proportion by weight of said polyol in said polyurethane is from about 2 to about 25 percent and said catheter is fabricated from an elastomeric polyurethane.

8. A medical dilatation balloon catheter in accordance with claim 7 wherein the amount of said polyol is within the range of about 4 to about 15 percent by weight based on the weight of said polyurethane.

9. A medical dilatation balloon catheter in accordance with claim 7 wherein the organic diisocyanate comprises 4,4'-methylenebis (phenyl isocyanate).

10. A medical dilatation balloon catheter in accordance with claim 7 wherein the chain extender comprises an aliphatic diol.

11. A medical dilatation balloon catheter in accordance with claim 10 wherein the chain extender is a mixture of 1,6-hexanediol and 1,4-cyclohexanedimethanol.

12. A medical dilatation balloon catheter in accordance with claim 7 wherein the chain extender is selected from the class consisting of 1,6-hexanediol, 1,4-cyclohexanedimethanol, Bisphenol A and mixtures of two or all of these compounds.

13. A medical dilatation balloon catheter in accordance with claim 7 which also comprises a flexible guide wire suitably mounted within said catheter.

14. A medical dilatation balloon in accordance with claim 1 wherein the organic diisocyanate comprises 4,4'-methylenebis (cyclohexylisocyanate).

15. A medical dilatation balloon catheter in accordance with claim 7 wherein the organic diisocyanate comprises 4,4'-methylenebis (cyclohexylisocyanate).

* * * * *